(12) United States Patent
Rahn

(10) Patent No.: US 7,819,817 B2
(45) Date of Patent: Oct. 26, 2010

(54) TEMPERATURE PROBE FOR INSERTION INTO THE ESOPHAGUS

(75) Inventor: Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 160 days.

(21) Appl. No.: 11/524,663

(22) Filed: Sep. 21, 2006

(65) Prior Publication Data

US 2007/0066968 A1    Mar. 22, 2007

(30) Foreign Application Priority Data

Sep. 21, 2005   (DE) .................. 10 2005 045 069

(51) Int. Cl.
*A61B 5/00* (2006.01)
(52) U.S. Cl. ...................................... 600/549
(58) Field of Classification Search .................. 600/549
See application file for complete search history.

(56) References Cited

U.S. PATENT DOCUMENTS

| | | | | |
|---|---|---|---|---|
| 5,161,536 | A | * | 11/1992 | Vilkomerson et al. ....... 600/443 |
| 5,368,564 | A | * | 11/1994 | Savage ..................... 604/95.04 |
| 6,156,254 | A | * | 12/2000 | Andrews et al. ............. 264/231 |
| 6,348,039 | B1 | | 2/2002 | Flachman et al. |
| 2002/0082515 | A1 | * | 6/2002 | Campbell et al. ........... 600/549 |
| 2002/0103445 | A1 | * | 8/2002 | Rahdert et al. .............. 600/549 |
| 2002/0115991 | A1 | | 8/2002 | Edwards |
| 2003/0135110 | A1 | * | 7/2003 | Leussler ..................... 600/422 |
| 2004/0024308 | A1 | * | 2/2004 | Wickline et al. ............ 600/422 |
| 2004/0034303 | A1 | * | 2/2004 | Korotko .................... 600/435 |
| 2004/0073132 | A1 | * | 4/2004 | Maahs et al. ................ 600/549 |
| 2004/0147852 | A1 | * | 7/2004 | Brister et al. ............... 600/549 |
| 2005/0090735 | A1 | * | 4/2005 | Carney et al. .............. 600/424 |
| 2005/0203382 | A1 | * | 9/2005 | Govari et al. .............. 600/424 |
| 2005/0251031 | A1 | * | 11/2005 | Smith ........................ 600/433 |
| 2005/0251032 | A1 | * | 11/2005 | Smith ........................ 600/433 |

FOREIGN PATENT DOCUMENTS

| | | |
|---|---|---|
| EP | 0 485 323 A1 | 5/1992 |
| WO | WO 97/41924 A1 | 11/1997 |
| WO | WO 00/27278 A1 | 5/2000 |

* cited by examiner

*Primary Examiner*—Max Hindenburg
*Assistant Examiner*—Michael C Stout

(57) ABSTRACT

The invention relates to a temperature probe for insertion into the human or animal body, having an unfoldable balloon on a catheter, on the outer skin of which balloon one or more temperature sensors is or are disposed. The catheter can be moved by way of a cable and according to one aspect of the invention an ultrasound sensor is disposed on its tip. Position sensors can also be provided on the outer skin of the balloon. The temperature probe is used to monitor the temperature distribution in the esophagus during a catheter ablation.

14 Claims, 7 Drawing Sheets

TEMPERATURE PROBE FOR INSERTION INTO THE ESOPHAGUS

CROSS REFERENCE TO RELATED APPLICATIONS

This application claims priority of German application No. 10 2005 045 069.5 filed Sep. 21, 2005, which is incorporated by reference herein in its entirety.

FIELD OF THE INVENTION

The invention relates to a temperature probe for insertion into the esophagus of the human or animal body. The temperature probe has a catheter with an unfoldable balloon, on the outer skin of which one or more temperature sensors are disposed. The invention also focuses on a catheter system with a computation module for processing the temperature data transmitted by the temperature probe and a hyperthermia device with a heat applicator to heat a tissue section in the heart and a temperature probe for insertion into the esophagus.

BACKGROUND OF THE INVENTION

To treat cardiac arrhythmia for example diseased areas of the heart are eradicated by means of catheter ablation in an electrophysiological intervention. In this process one or more catheters are first inserted into the relevant ventricle for electrophysiological mapping of the cardiac wall. When the diseased area has been located, it is eradicated using an ablation catheter with a heat-generating high-frequency current. It is possible to treat cardiac arrhythmia permanently in this manner.

Electro-anatomical mapping systems, such as the Carto-System from Biosense Webster, Diamondbar, Calif., USA, are used in this process to visualize the ablation catheter during the ablation procedure in a representation of the cardiac anatomy. The Carto-System includes a position sensor contained in the ablation catheter and a location device positioned below the patient. This comprises three transmitters of electromagnetic radiation, which is picked up by the position sensor and allows said position sensor to be located to an accuracy of up to 1 mm.

There is however the risk with ablation that adjacent tissue areas may be irreparably damaged. When treating atrial fibrillation, ablation at the posterior wall of the left atrium can for example cause perforation in the esophagus, if the ablation is carried out in the vicinity of the esophagus, which is adjacent to the epicardium. Ablation in the vicinity of the pulmonary veins that open into the left atrium can also cause stenosis of the pulmonary veins.

There is therefore cause to insert a temperature probe into the esophagus, to monitor the temperature in the esophagus during the ablation procedure. If the temperature increases, the ablation could be stopped or the power output of the ablation catheter could be reduced, to prevent damage to the esophagus. However there are as yet no temperature probes, which are ideally suited for such an application.

A temperature probe for insertion into a body lumen, in particular a blood vessel, is known from US 2004/0147852 A1. This has a balloon catheter, on the outside of which temperature sensors can be disposed. When the balloon is inflated, the temperature sensors are pushed onto the inside of the blood vessel and can therefore measure the temperature at the vessel wall very accurately. This is used to identify inflammatory plaque. The balloon catheter is also provided with x-ray visible markers for better visibility in the x-ray image.

US 2002/0115991 A1 describes a device for thermal treatment of the esophagus, in particular the mouth of the esophagus. The heat-emitting elements, for example electrodes, are disposed on the outer skin of an inflatable balloon element, to be brought into direct contact with the sphincter muscle to be treated. The balloon element can be deflected by a cable. Temperature sensors can also be disposed on the balloon element in addition to the electrodes. Parts of the device are optionally configured to be x-ray visible, so that said device is visible on fluoroscopy images and the intervention can be effectively controlled as a result.

WO 00/27278 describes a further thermosensor for insertion into blood vessels, wherein temperature sensors are disposed on the outside of an inflatable balloon element.

A thermosensor for the rectum is known from U.S. Pat. No. 6,348,039, which similarly has an inflatable balloon element, to the outside of which at least one temperature sensor is attached. This is used during hyperthermia treatment of prostate cancer to control temperature changes in the prostate.

EP 0 485 323 A1 similarly discloses the use of a temperature probe during hyperthermia treatment of the prostate. A heat applicator is inserted into the rectum and a catheter with the temperature probe is inserted into the urethra. The catheter contains a balloon, which is inflated in the bladder, to fix the position of the catheter end in relation to the prostate. Means for measuring the distance between the heat applicator and the temperature probe are similarly provided.

WO 97/41924 describes a catheter for hyperthermia treatment of the womb. This comprises a balloon catheter, to the outer skin of which both antennas for electromagnetic radiation and also temperature sensors are attached. After insertion into the womb, the balloon is inflated, such that the antennas and temperature sensors are pushed onto the inner wall of the uterus.

SUMMARY OF THE INVENTION

The invention has the object of developing a temperature probe of the type mentioned in the introduction, such that it can be using during cardiac catheter ablation procedures to monitor the temperature in the esophagus.

According to a first aspect the invention achieves this object with the features of the claims. According to this the catheter can be moved by a cable, to change the position of the esophagus in the body of the patient. This serves to move the esophagus away from the heart, when too high a temperature is detected in the esophagus during catheter ablation, for example at points of the left atrium when treating atrial fibrillation. The inventive temperature probe therefore does not only provide temperature information, it can also implement appropriate measures to protect the esophagus. Once the esophagus has been displaced, it is possible to ablate with the required energy, without running the risk of esophageal fistulas.

According to a second aspect the invention achieves the object in that an ultrasound sensor is disposed on the tip of the catheter. Ultrasound catheters for insertion into the esophagus are already known and are referred to inter alia as TEE (TransEsophageal Echocardiogram) catheters. Combination with a temperature probe has the advantage that the temperature in the esophagus can be measured at the same time, while the ultrasound sensor is used to determine position and distance from a heat applicator or ablation catheter in the ventricle. The ultrasound sensor can therefore give a first indication of when the distance drops below a specified distance and it is therefore possible that a critical temperature threshold will be exceeded in the esophagus.

The inventive temperature probe also has an unfoldable balloon, on the outer skin of which one or more temperature sensors are disposed. This allows the temperature probe, after it has been inserted for example by way of the catheter into the body, to unfold or inflate in the manner of a balloon, such that the outer skin with the temperature sensors is as close as possible to the wall of the esophagus. The temperature sensors therefore do not measure the temperature changes in the lumen but the temperature changes in the esophageal wall, which are of actual relevance. This allows accurate acoustic, optical or tactile feedback to the electrophysiologist, when a temperature change is determined in the esophageal wall.

The catheter with the unfoldable balloon is preferably so flexible that it can be inserted into the esophagus by means of swallowing movements by the patient. This is very advantageous, as the temperature probe can be inserted in this manner into a patient, who is not under local or general anesthesia. In the prior art, it was necessary until now, as described in US 2002/0115991, for the esophagus to be anesthetized locally, in order to insert a catheter into the esophagus. However it is very difficult to administer local anesthesia in the region of the esophagus and general anesthesia involves a certain degree of risk for the patient. Also during catheter ablations the patient is generally only sedated but should remain conscious.

The outer skin of the balloon is preferably such that it can be easily swallowed by the patient and can therefore be transported by swallowing movements into the esophagus and from there further on toward the stomach. To this end the outer skin preferably has a slightly rough surface structure but is generally extremely flexible and soft. The outer skin is preferably made of processed or unprocessed rubber.

The catheter with the balloon can therefore preferably be inserted trans-orally or trans-nasally.

The balloon can preferably be filled with a gas, for example air, for unfolding purposes.

The catheter and/or balloon is/are preferably equipped with x-ray visible markers for precise positioning. This makes it possible to position the balloon in the esophagus under x-ray control, such that it is located in the most optimum manner possible on the adjacent epicardial tissue of the left atrium of the heart. During an ablation procedure the patient can therefore convey the catheter into the stomach initially by means of swallowing movements. The electrophysiologist then withdraws the catheter, until the x-ray visible markers are in the direct vicinity of the left atrium of the heart. To this end a contrast agent can optionally be briefly supplied to the left atrium.

The x-ray visible markers preferably comprise one or more thin wires, which are wound for example around the outer skin of the balloon or the catheter sheath. This allows the marker to have a spiral or annular form, which extends at least over part of the balloon or catheter.

In one preferred embodiment one or more position sensors is/are also disposed on the outer skin of the balloon. These can operate for example according to the same principle as the Carto-System, such that the position of the temperature probe can be measured in the known manner. With this embodiment the wall contact of the position sensors preferably allows the 3D form of the inside wall of the relevant hollow organ, in particular the esophagus, to be reproduced. For example triangulation between the detected position sensors can be used to reconstruct a relatively smooth surface of the esophagus with the aid of mesh generators. The "marching cube" algorithm for example can be used for this. The temperature measured by the temperature sensors can be marked, preferably with color coding, on the sleeve-type 3D form of the esophagus. The temperature values between the temperature probes can for example be interpolated, such that there is a continuous color pattern. The temperature and position sensors can be used in this manner for locally precise measurement of the temperature in the esophagus.

Both the temperature and position sensors are preferably attached to a mesh enclosing the outer skin of the balloon. Any other sort of attachment is however possible, where the sensors are pushed outward when the balloon unfolds.

The temperature probe described above is preferably part of a catheter system with a catheter for insertion of the temperature probe into the esophagus and a computation module to process the temperature and optionally also position data transmitted by the temperature probe. The catheter system preferably also comprises a screen to display the temperature distribution in the esophagus, in particular to display the inside wall of the esophagus with temperature color coding, as described above.

It is particularly preferable for the temperature probe to be part of a hyperthermia device to heat a tissue section in the heart, in particular to eradicate a diseased region in the heart by catheter ablation, having a heat applicator that can be positioned in the vicinity of the tissue section to heat said tissue section and a temperature probe that can be unfolded in the manner of a balloon for insertion into a vessel or hollow organ, namely the esophagus, located in the vicinity of the tissue section. The hyperthermia device is in particular an ablation system, the heat applicator correspondingly an ablation catheter.

The hyperthermia device preferably has a mapping system to determine the position of the heat applicator and the temperature probe, in order to be able to measure the relative position and distance between the two.

According to one preferred embodiment the hyperthermia device also has a computation module to process the temperature data transmitted by the temperature probe and the position data transmitted by the mapping system, as well as a screen to display the relative position of the heat applicator to the vessel or hollow organ or to display the temperature distribution in the vessel or hollow organ.

The hyperthermia device preferably also has a warning facility, which generates an acoustic, tactile or optical warning signal when a predetermined temperature measured in the vessel or hollow organ is exceeded or when the distance between the heat applicator and the temperature probe drops below a predetermined distance. Alternatively the power output of the heat applicator can also be reduced or stopped.

BRIEF DESCRIPTION OF THE DRAWINGS

The invention is described below based on preferred exemplary embodiments with reference to the accompanying drawings, in which.

DETAILED DESCRIPTION OF THE INVENTION

Figure 1:
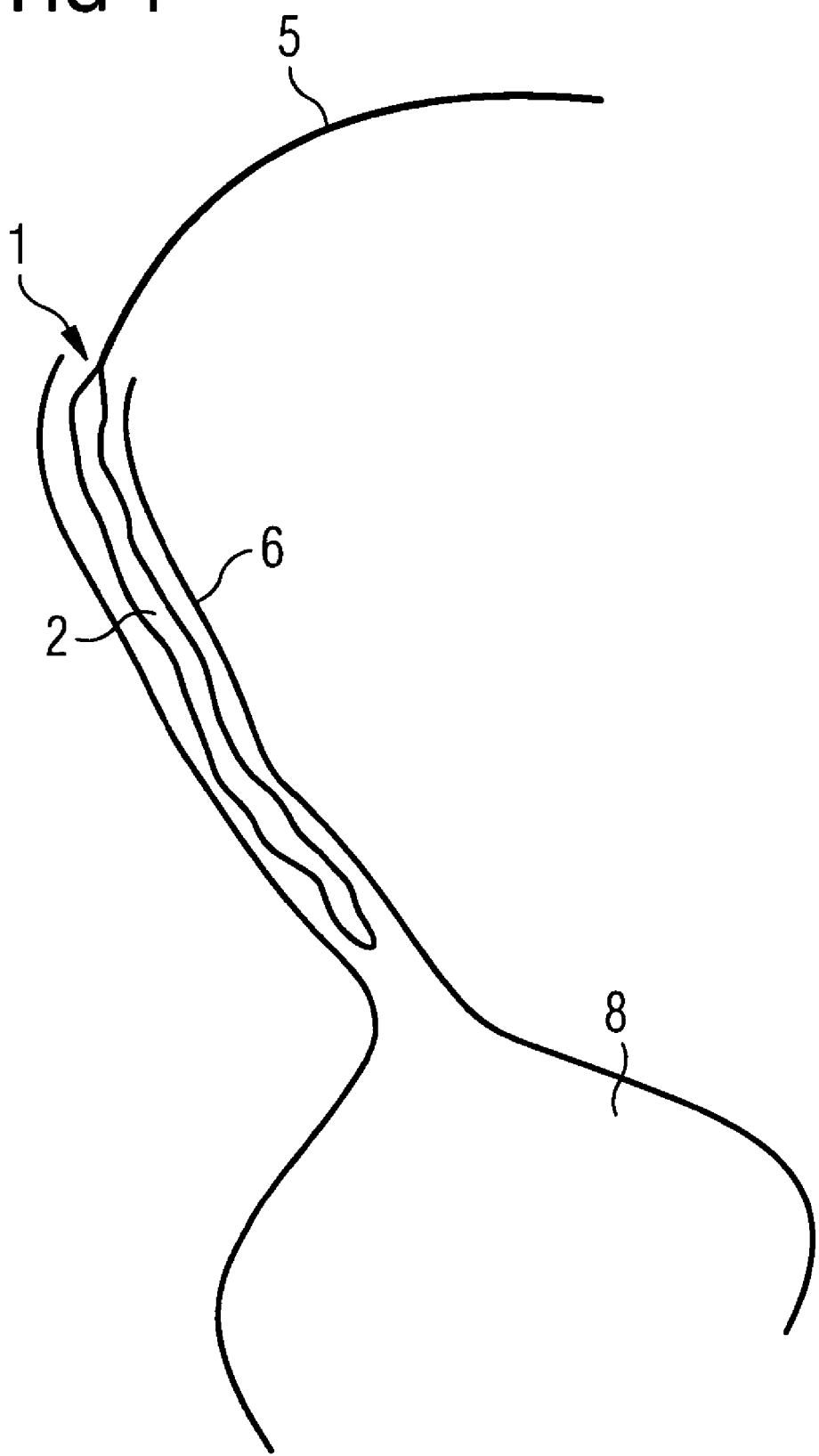
FIG. 1 shows a schematic diagram of a temperature probe in the esophagus.

FIG. 1 shows a schematic diagram of an esophagus 6 opening into a stomach 8. Inserted into this is a catheter 5 with a temperature probe 1 with an unfoldable balloon 2. The drawing shows the balloon 2 in the folded state, in which it is inserted by way of the catheter 5 into the esophagus 6. This is preferably achieved by means of swallowing movements by the patient.

Figure 2:
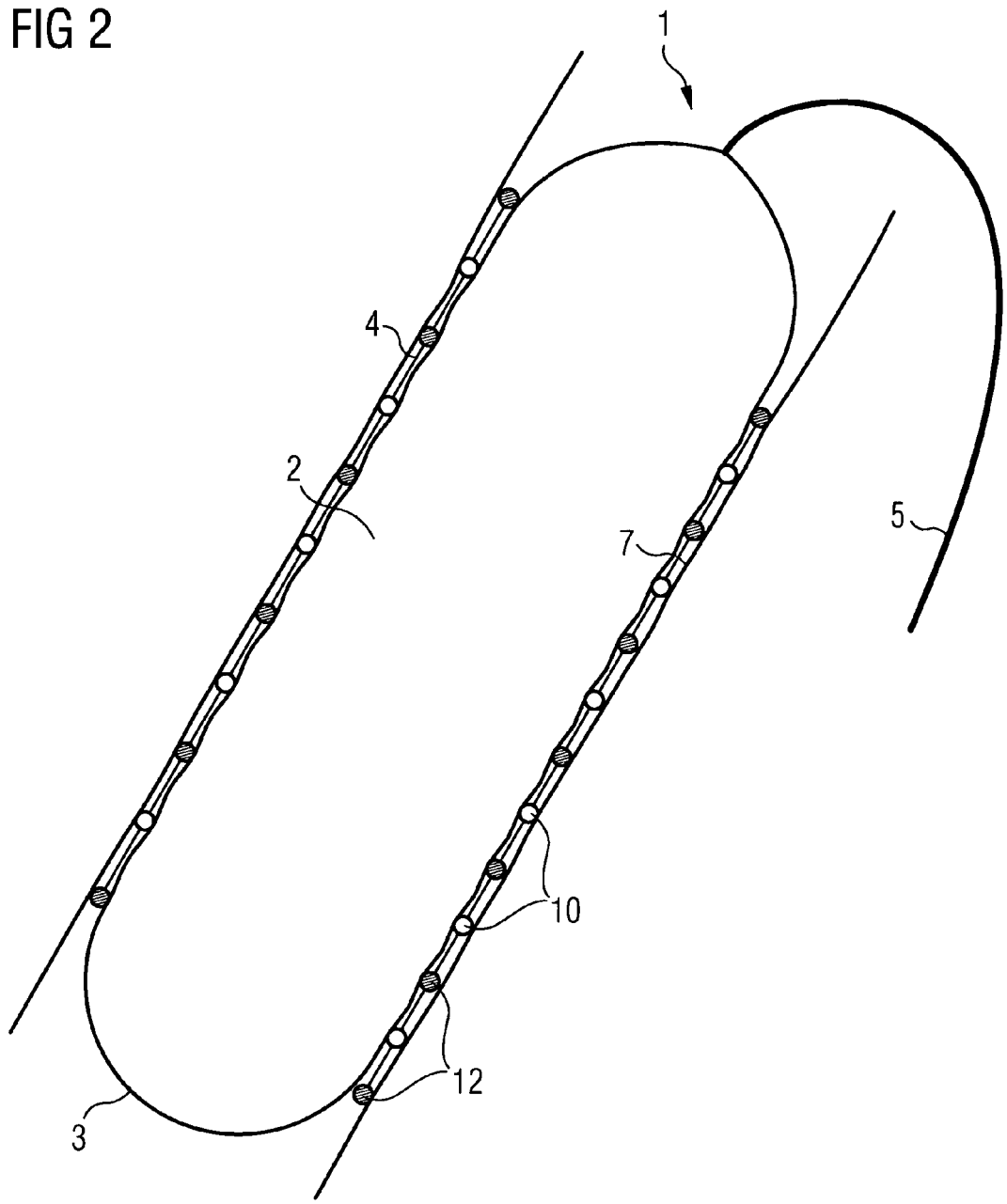
FIG. 2 shows a cross-section through a first exemplary embodiment of the inventive temperature probe with an unfoldable balloon.

FIG. 2 shows the temperature probe 1 enlarged and in cross-section and in the unfolded state 5 again shows the catheter, which for example contains a flexible tube, by way of which air can be supplied to inflate the balloon 2. The gas-filled balloon 2 is enclosed by an outer skin 3, made of an elastic plastic for example. A number of temperature sensors 10 and position sensors 12 are disposed on the outer skin 3, being pushed by the balloon 2 onto the wall 7 of the esophagus 6. The sensors 10, 12 can be attached in any manner to the outer skin; they can also be inside the balloon 2, as long as there is adequate thermal contact between them and the wall of the hollow organ. In the example shown the temperature and position sensors 10, 12 are integrated into a fine lattice structure 4, which connects the sensors 10, 12 and is pushed with the sensors onto the wall 7 of the esophagus when the balloon 2 unfolds. The lattice structure 4 an be a fine net, in which the electric wires for connecting the position and temperature sensors 10, 12 can also be integrated.

In the example shown the individual temperature sensors 10 are provided at short intervals of approx. 0.5 to 5 mm. The number of position sensors 12 corresponds roughly to the number of temperature sensors 10. Embodiments are however also possible, in which there is provision for fewer position sensors 12, for example only a single position sensor, or in which the number of temperature sensors 10 is similarly very much lower. For example just one annular region or an elongated radial section of the balloon 2 could be equipped with the temperature sensors 10.

Figure 3:
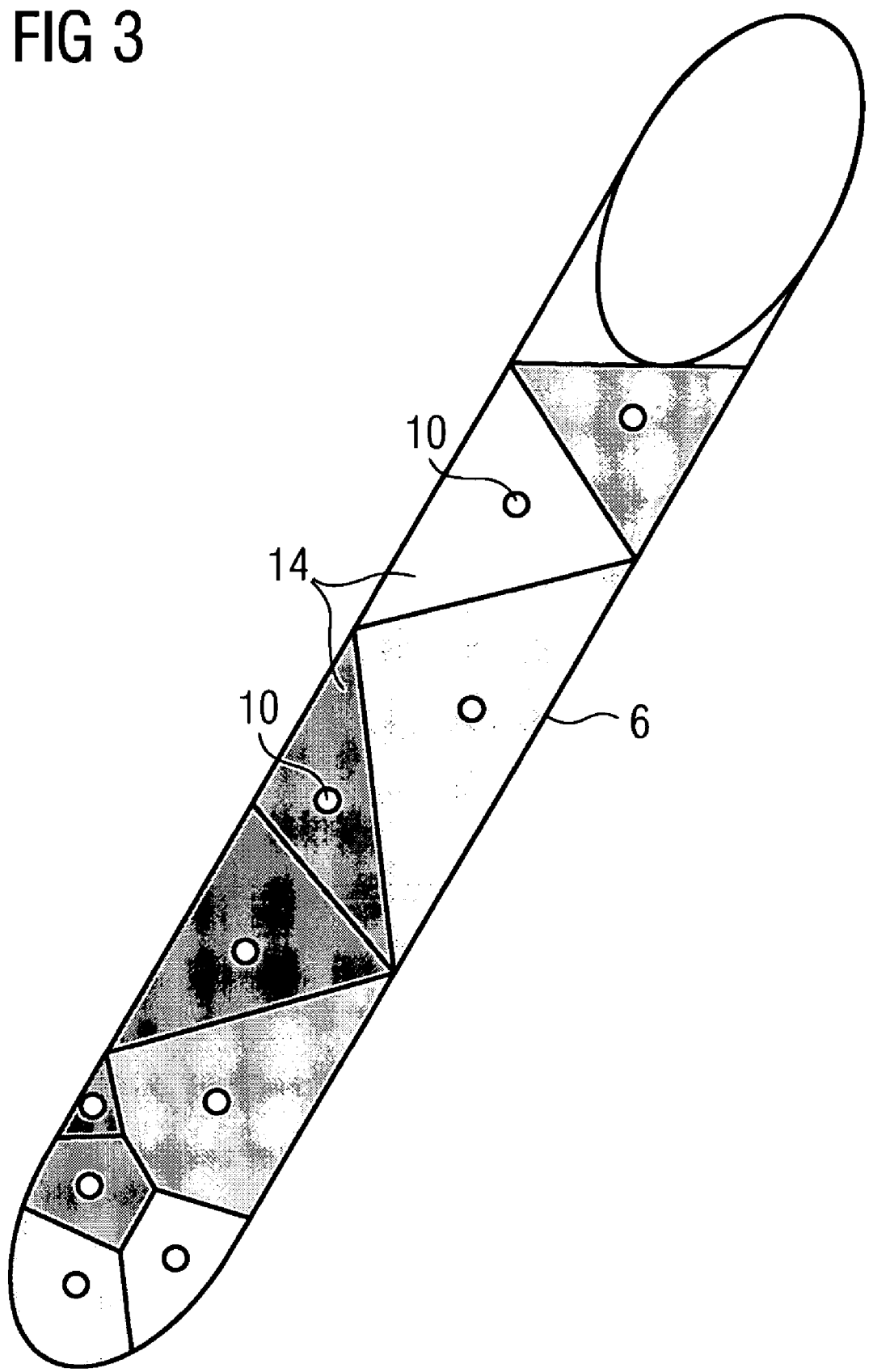
FIG. 3 shows an example of a diagram of the temperature distribution in the esophagus.

FIG. 3 shows an example of a diagram of a temperature distribution in the esophagus 6. Each temperature sensor 10 is enclosed by a polygonal segment 14, the coding of which is determined by the temperature value measured by the associated temperature sensor. The positions of the individual segments in the space are preferably determined by way of their spatial relationship to the known positions of the position sensors 12. The temperature is preferably shown color-coded but in the example shown different gray values are selected instead.

The diagram in FIG. 3 shows a perspective view of the esophagus 6, with the individual segments 14 each colored in a gray shade according to the temperature prevailing there. In another embodiment the wall 7 of the esophagus 6 can however also be shown flattened out in one plane, so that no regions are covered by others. The color or gray value distribution of the surface can also be smoothed, so that the color and gray value transitions are gradual. This can be done either by interpolating the temperature values between the temperature sensors or by smoothing the resulting temperature map.

It should be noted that the creation of the visual display of the temperature distribution, for example according to FIG. 3, is not necessarily associated with the condition that the temperature probe 1 is also equipped with position sensors 12. Instead the known distribution of the temperature sensors 10 around the balloon could also be used to determine and optionally to display the temperature distribution along the lumen wall 7. The temperature sensors 10 can also be displayed using imaging methods such as ultrasound or on x-ray images and their position determined in this manner.

Figure 4:
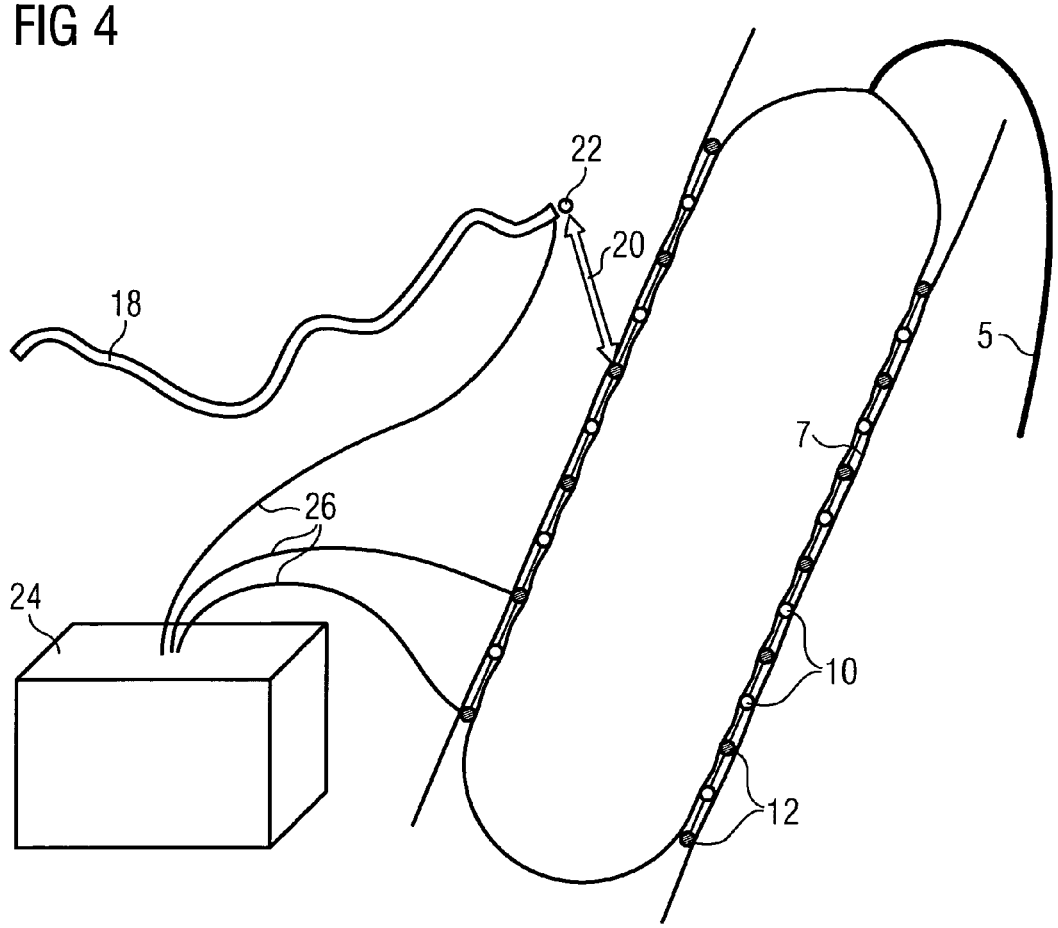
FIG. 4 shows a schematic diagram of an ablation system with mapping system for position determination.

FIG. 4 finally shows the temperature probe shown in FIG. 2 as part of a hyperthermia device, in particular an ablation system. This includes a temperature probe 1, which is inserted by way of the catheter 5 into the esophagus and unfolded such that the temperature sensors 10 and position sensors 12 are pushed by the balloon 2 onto the wall 7 of the esophagus 6. In addition to the temperature probe 1 the ablation system also contains an ablation catheter 18, on the tip of which an ablator is disposed to eradicate tissue. This is inserted into the heart for example by way of the inguinal vein or artery. A position/orientation sensor 22 is similarly disposed on the tip of the catheter. This sensor can be used to scan the inside wall of the heart and optionally to carry out an electrophysiological examination. The position/orientation sensor 22 and the position sensors 12 of the temperature probe are connected by way of the connecting cables 26 to a mapping system 24. These connecting cables are preferably fed through the corresponding catheters 5, 18, contrary to the diagram. The mapping system 24 can for example be the Carto-System from Biosense Webster or a comparable system. For example the mapping system can also operate with the aid of magnets disposed below the patient, which generate a magnetic field in the examination region, said magnetic field being acquired by the various position sensors 12, 22. This allows the distance 20 between the position sensor 22 of the ablation catheter and the wall 7 of the esophagus to be determined and ablation can optionally be terminated, if this distance drops below a predetermined value. Alternatively the mapping system can emit a warning signal in this instance.

In one specific embodiment of the temperature mapping the individual temperature sensors can be read out with relative time delays. This allows time-variant temperature mapping to take place, by means of which a time-dependent change in tissue temperature can be visualized. The delay interval can be defined by the user. This makes it possible to eliminate a known time delay, for example in the temperature increase, from the measured data, to facilitate data evaluation.

Figure 5:
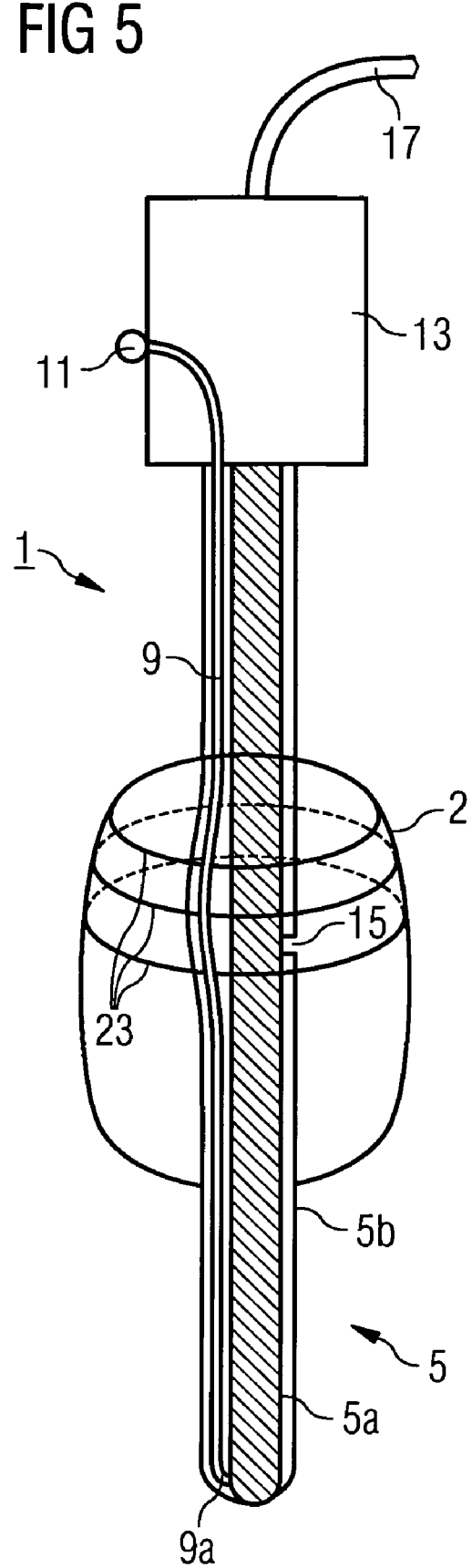
FIG. 5 shows a schematic cross-section through a temperature probe according to a second embodiment.

The principle of the movable catheter is to be described in more detail below with reference to FIGS. 5 and 6. FIG. 5 shows a temperature probe 1 with an inflatable balloon 2, to the outer skin of which temperature sensors and optionally also position sensors (not shown) are attached, as described in more detail above.

FIG. 5 shows the catheter 5 in more detail. It comprises a body 5a and a sheath 5b, which for example comprises a thin plastic sleeve around the body 5a. The body 5a itself is as thin and flexible as possible, so that the catheter 5 and the balloon 2 can be inserted into the esophagus by means of swallowing movements by the patient. Essentially the body 5 only has to contain a small, thin, flexible tube, through which a gas, for example air, can be introduced into the balloon 2 through the air passage 15 to unfold it in the air pipe [sic]. The air is fed in from the outside by way of a supply tube 17, for example from a pressurized air tank.

The catheter 5 can be operated, for example be inserted into the esophagus and moved, by way of a handpiece 13. To this end a cable 9 is provided in the example shown. This essentially comprises an extremely thin string 9, for example a tear-resistant nylon thread or a thin wire, which is attached at the distal end of the catheters at the point 9a on its body and is fed between the catheter sheath 5b and its body 5a to the handpiece 13. There the cable 9 is connected to an operating element 11, for example a button or loop, on which the operator (e.g. an electrophysiologist) pulls gently, to deform the catheter 5, in particular to bend it and therefore deflect it. While FIG. 5 shows the catheter in its extended state, in FIG. 6 it is bent by tightening the cable 9 at the point 19. How the catheter 5 deforms, depends both on the attachment point 9a of the cable 9 to the body 5a and also the structure of the catheter body 5a, which has certain intended buckling points under certain circumstances.

If the catheter 5 is to be bent or deformed in different directions and in a different manner, it is expedient to provide a number of cables 9. In particular a number of thin strings 9 can be disposed at different points 9a along the periphery and along the length of the catheter body 5a. It is then possible to bend the catheter in different directions by pulling on these different strings.

The purpose of the cables 9 is to deform the catheter so significantly at a specific point that it moves the esophagus away from the ablation point within the body. To this end the catheter must have a certain mechanical stability. The balloon 3 can for example contribute to this, if it is configured to be correspondingly long and therefore extends over a substantial part of the catheter 5 (not shown). When the balloon 3 is inflated, it brings about a certain rigidity or stability of the temperature probe (1), such that said temperature probe 1 can be moved by the operator at the handpiece 13 such that the esophagus 6 is moved too. Such an elongated balloon 3 does not have to be fitted with temperature sensors 10 along its entire length.

According to another embodiment the necessary mechanical stability of the catheter 5 can also be achieved by increasing the pressure in the catheter lumen. The catheter lumen can for example be a tube in the catheter or even the intermediate space between the catheter body 5a and its sheath 5b. The pressure can be increased by feeding in pressurized air by way of the supply tube 17. Alternatively a fluid can also be pumped into the catheter lumen. The increased pressure of the medium in the catheter lumen increases its rigidity and mechanical stability, such that it can be used to displace the esophagus.

According to yet a further embodiment the esophagus can be displaced with the catheter 5 by providing a number of cables 9 on the same side of the catheter 5, which are however attached to points 9a on the body 5 of the catheter 5 distributed along its length (not shown). If all these strings 9 are tightened at the same time, for example using a corresponding operating element 11, the handpiece 13, the catheter is moved completely to the side, on which the strings are attached. The buckling point of the catheter is thus directly at the handpiece. This allows a distal section of the catheter to be moved a relatively large distance. This embodiment with a number of strings can of course be combined with the above-mentioned embodiment of an elongated balloon 2 or the pressure increase in the catheter lumen. The combination produces a mechanically stable catheter, which can be deflected in a specific direction directly at the handpiece 13.

Figure 6:
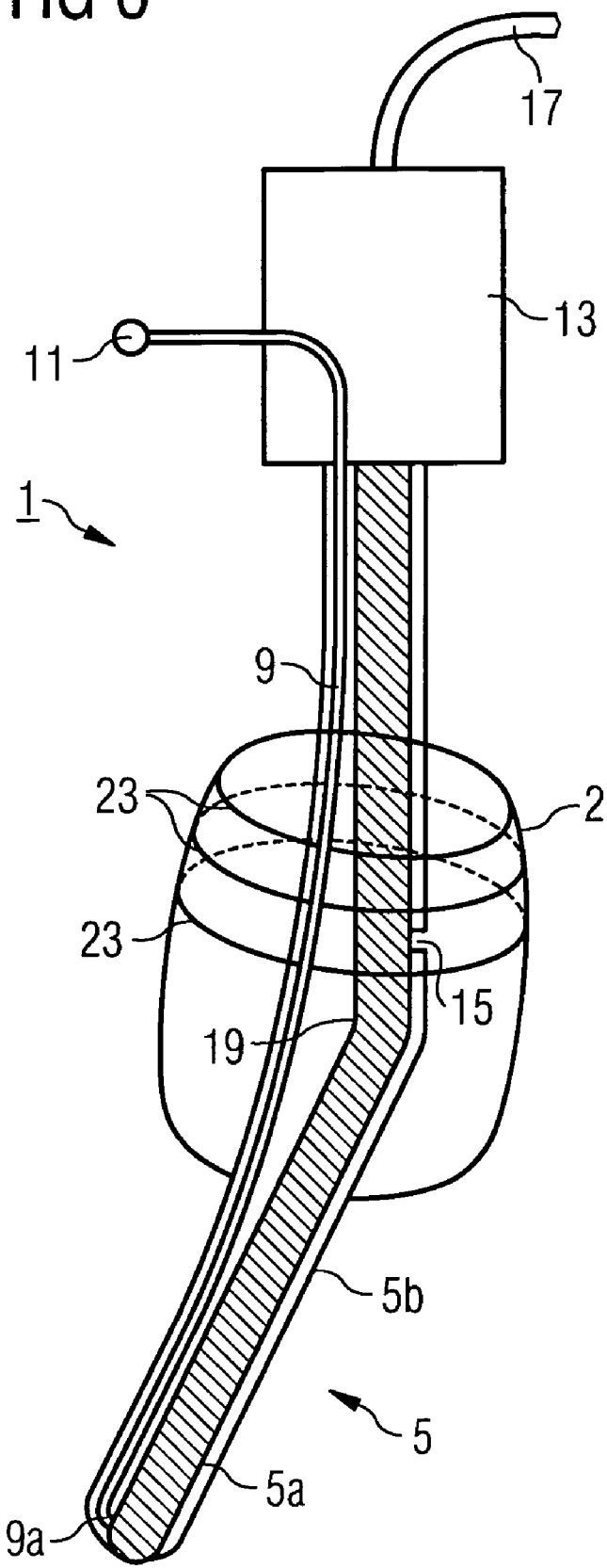
FIG. 6 shows a schematic cross-section through the temperature probe in FIG. 5, with deflected catheter.

FIGS. 5 and 6 show a further optional feature of the temperature probe again, namely the x-ray visible markers 23. In the example shown these are formed respectively by annular wires, etc., which are fed round the balloon 2. It is particularly preferable for the x-ray visible markers to comprise a thin spiral wire made of metal or another x-ray proof material. This spiral can either be disposed outside on the outer skin 3 of the balloon 2 or inside the balloon 2. Alternatively the body 5a or sheath 5b of the catheter can have such a spiral wound round it (not shown).

Figure 7:
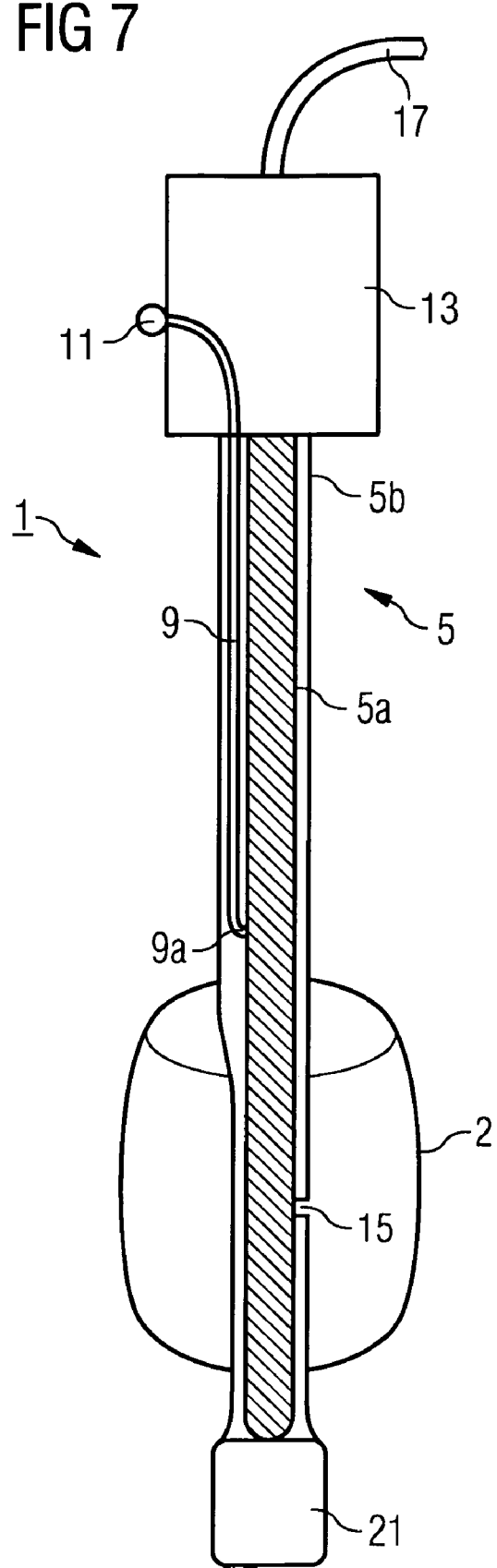
FIG. 7 shows a schematic cross-section through a temperature probe according to a third embodiment of the invention.

FIG. 7 shows a further embodiment still, wherein an ultrasound probe 21 is disposed at the distal end of the catheter 5. Otherwise the temperature probe 1 in FIG. 7 essentially corresponds to the ones in FIGS. 5 and 6, the same parts being marked with the same reference characters. Only the cable 9 is attached to a less distal point 9a on the body 5a of the catheter 5. This means that when the cable 9 is tightened, the catheter 5 is bent at a more proximally disposed point. This facilitates displacement of the esophagus in the event of too high a temperature being detected by the temperature sensors 10 on the balloon 2 and the esophagus therefore having to be displaced from the ablation point.

The ultrasound probe 21 is a probe, which is typically used for TEE ("Transesophageal Electrocardiogram") examinations. Such probes are therefore known to the person skilled in the art and do not have to be described in more detail here.

The combination of TEE with a temperature measurement by means of a balloon-type temperature probe also has the advantage that the balloon 2 can be positioned in an optimum manner with the aid of the ultrasound probe 21. There is therefore no need for position sensors 12 on the outer skin 3 of the balloon 2 in the embodiment in FIG. 7.

The invention claimed is:

1. A temperature probe that inserts into an esophagus of a patient for protecting the esophagus in a medical procedure, comprising:
   a catheter;
   a balloon disposed on the catheter;
   a plurality of temperature sensors disposed on an outer skin of the balloon that monitor the temperature of the esophagus;
   a plurality of cables connected to the catheter at different points along a periphery and along a length of the catheter that moves the catheter to change a position of the esophagus in a body of the patient according to the monitored temperature; and
   a plurality of position sensors disposed on the outer skin of the balloon to determine a position of the temperature probe,
   wherein both the temperature sensors and the position sensors are attached to a mesh enclosing the outer skin of the balloon;
   wherein upon the balloon being supplied with air to an inflated position, the plurality of temperature sensors and the plurality of position sensors are attached to the mesh in an alternating arrangement in which each temperature sensor is positioned adjacent to one of the position sensors and each position sensor is positioned adjacent to one of the temperature sensors.

2. The temperature probe as claimed in claim 1, wherein an ultrasound sensor is disposed on a tip of the catheter to determine a position of the temperature probe.

3. The temperature probe as claimed in claim 1, wherein an x-ray visible marker is disposed on the outer skin of the balloon to control a position of the balloon in the esophagus.

4. The temperature probe as claimed in claim 3, wherein the x-ray visible marker is a thin and flexible wire wound around the outer skin of the balloon.

5. The temperature probe as claimed in claim 1, wherein the catheter is flexible and is swallowed into the esophagus by the patient.

6. The temperature probe as claimed in claim 1, wherein the balloon is inflated by a gas after inserting into the esophagus so that the temperature sensor contacts with an inside wall of the esophagus.

7. The temperature probe as claimed in claim 1, wherein the mesh comprises an x-ray visible marker disposed on the outer skin of the balloon.

8. The temperature probe as claimed in claim 1, wherein the medical procedure is a cardiac catheter ablation procedure.

9. The temperature probe as claimed in claim 1, wherein the plurality of temperature sensors and the plurality of position sensors sensors are integrated into a fine lattice structure, the lattice structure including a plurality of electric wires to connect the respective plurality of temperature sensors and plurality of position sensors within the lattice structure.

10. A temperature probe that inserts into an esophagus of a patient for protecting the esophagus in a medical procedure, comprising:
   a catheter;
   a balloon disposed on the catheter;
   a plurality of temperature sensors disposed on an outer skin of the balloon that monitor the temperature of the esophagus;
   a plurality of cables connected to the catheter at different points along a periphery and along a length of the catheter that moves the catheter to change a position of the esophagus in a body of the patient according to the monitored temperature; and
   a plurality of position sensors disposed on the outer skin of the balloon to determine a position of the temperature probe,
   wherein both the temperature sensors and the position sensors are attached to a mesh enclosing the outer skin of the balloon;
   a computation unit connected to the temperature probe that calculates a temperature distribution in the esophagus by processing a data of the monitored temperature; and
   a screen that displays the temperature distribution in the esophagus;
   wherein upon the balloon being supplied with air to an inflated position, the plurality of temperature sensors and the plurality of position sensors are attached to the mesh in an alternating arrangement in which each temperature sensor is positioned adjacent to one of the position sensors and each position sensor is positioned adjacent to one of the temperature sensors.

11. The catheter system as claimed in claim 10, wherein the temperature distribution is a temperature distribution in an inside wall of the esophagus and the screen displays the temperature distribution with a temperature color coding.

12. The catheter system as claimed in claim 10, wherein the temperature probe comprises a position sensor to determine a position of the temperature probe.

13. The catheter system as claimed in claim 12, wherein the computation unit processes a position data transmitted by the temperature probe.

14. The temperature probe as claimed in claim 10, wherein the plurality of temperature sensors and the plurality of position sensors sensors are integrated into a fine lattice structure, the lattice structure including a plurality of electric wires to connect the respective plurality of temperature sensors and plurality of position sensors within the lattice structure.

* * * * *